US011850371B2

(12) United States Patent
Colgan et al.

(10) Patent No.: US 11,850,371 B2
(45) Date of Patent: Dec. 26, 2023

(54) PROSTHETIC DELIVERY DEVICE TRAYS, PACKAGING SYSTEMS AND METHODS

(71) Applicant: Medtronic, Inc., Minneapolis, MN (US)

(72) Inventors: Larry C. Colgan, Geyserville, CA (US); John M. Gallagher, Roscam (IE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/719,775

(22) Filed: Apr. 13, 2022

(65) Prior Publication Data

US 2023/0014376 A1 Jan. 19, 2023

Related U.S. Application Data

(60) Provisional application No. 63/221,193, filed on Jul. 13, 2021.

(51) Int. Cl.
*A61M 25/00* (2006.01)
*A61B 50/33* (2016.01)
*A61F 2/00* (2006.01)

(52) U.S. Cl.
CPC .......... *A61M 25/002* (2013.01); *A61B 50/33* (2016.02); *A61F 2/0095* (2013.01)

(58) Field of Classification Search
CPC ..... A61M 25/002; A61B 50/33; A61F 2/0095
USPC ............................................... 206/571, 364
See application file for complete search history.

(56) References Cited

U.S. PATENT DOCUMENTS

| | | | | |
|---|---|---|---|---|
| 4,160,505 A | * | 7/1979 | Rauschenberger | .... A61B 50/33 206/571 |
| 4,925,448 A | * | 5/1990 | Bazaral | ............... A61M 25/002 206/370 |
| 5,318,543 A | * | 6/1994 | Ross | .................... A61J 15/0023 604/170.01 |
| 5,848,691 A | * | 12/1998 | Morris | ................ A61M 25/002 206/364 |
| 5,947,284 A | * | 9/1999 | Foster | .................... A61B 50/30 206/364 |

(Continued)

FOREIGN PATENT DOCUMENTS

EP    1067885 A2    1/2001

OTHER PUBLICATIONS

Extended European Search Report, EP Application No. 22181818.0, dated Nov. 11, 2022, 13 pages.

*Primary Examiner* — Jacob K Ackun
(74) *Attorney, Agent, or Firm* — Medler Ferro Woodhouse & Mills PLLC (57) ABSTRACT

Trays and packaging systems for a prosthesis delivery device that permit conversion from a packaged, storage/or shipping configuration to a loading configuration for the loading of a prosthesis. The prosthesis may be a prosthetic heart valve. In the packaged configuration, the delivery device can be supported within the tray, which includes a recess and at least one clip maintaining the delivery device within the recess. In the loading configuration, the delivery device can be arranged for loading of the prosthesis within a bath area of the tray. Optionally, the delivery device can be stored in the packaged configuration in a U-shape. Some embodiments include an additional recess for positioning an indeflator fluid line or tubing. Methods of use are also disclosed.

20 Claims, 8 Drawing Sheets

(56) References Cited

U.S. PATENT DOCUMENTS

| | | | | |
|---|---|---|---|---|
| 5,947,296 | A * | 9/1999 | Castora | A61M 25/002 206/466 |
| 6,068,121 | A * | 5/2000 | McGlinch | A61M 25/002 206/364 |
| 6,907,992 | B2 * | 6/2005 | McMichael | A61B 50/33 206/370 |
| 8,584,849 | B2 | 11/2013 | McCaffrey | |
| 8,662,306 | B2 * | 3/2014 | Agrawal | A61M 25/002 206/370 |
| 8,960,432 | B2 * | 2/2015 | Agrawal | B65B 63/04 206/364 |
| 9,022,212 | B2 * | 5/2015 | Spaargaren | A61M 25/002 206/364 |
| 9,486,604 | B2 | 11/2016 | Murray et al. | |
| 9,827,063 | B1 * | 11/2017 | Barnell | B65D 25/10 |
| 10,350,047 | B2 | 7/2019 | Rajpara et al. | |
| 10,729,541 | B2 | 8/2020 | Francis et al. | |
| 2004/0243214 | A1 * | 12/2004 | Farrell | A61F 2/0095 206/370 |
| 2006/0011501 | A1 * | 1/2006 | Itou | A61M 25/002 206/370 |
| 2007/0197998 | A1 * | 8/2007 | Itou | A61B 50/24 604/523 |
| 2014/0110296 | A1 * | 4/2014 | Terzibashian | B65D 25/108 206/438 |
| 2015/0068941 | A1 * | 3/2015 | Caron | A61M 25/002 206/364 |
| 2015/0129456 | A1 * | 5/2015 | Miller | A61B 46/10 206/571 |
| 2015/0196391 | A1 | 7/2015 | Dwork | |
| 2016/0045718 | A1 * | 2/2016 | Pruitt | A61M 25/10182 604/97.02 |
| 2017/0056149 | A1 | 3/2017 | Rajpara et al. | |
| 2017/0340787 | A1 * | 11/2017 | Corbett | A61M 25/002 |
| 2018/0110578 | A1 | 4/2018 | Gallagher | |
| 2018/0250495 | A1 * | 9/2018 | McNabb | A61M 25/002 |
| 2019/0076207 | A1 * | 3/2019 | Hays | A61B 50/33 |
| 2020/0345489 | A1 * | 11/2020 | Duffy | A61F 2/2436 |
| 2022/0387750 | A1 * | 12/2022 | Hendrickson | A61M 25/002 |

* cited by examiner

PROSTHETIC DELIVERY DEVICE TRAYS, PACKAGING SYSTEMS AND METHODS

CROSS-REFERENCE TO RELATED APPLICATIONS

This Non-Provisional patent application claims the benefit of the filing date of U.S. Provisional Patent Application Ser. No. 63/221,193, filed Jul. 13, 2021, entitled "PROSTHETIC DELIVERY DEVICE TRAYS, PACKAGING SYSTEMS AND METHODS," the entire teachings of which are incorporated herein by reference.

FIELD

The present technology is generally related to trays and packaging systems for a delivery device configured to deliver a prosthesis. In some examples the delivery device is configured for transfemoral delivery of a stented prosthetic heart valve. Methods of using the trays and packaging systems are also disclosed.

BACKGROUND

This disclosure relates to trays, packaging systems and method for delivery devices and components for a transcatheter stented prosthesis, such as a stented prosthetic heart valve.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter of the delivery device, inserted inside a body lumen of the patient, such as the femoral artery, and delivered to a desired location in the heart where the valve prosthesis is then deployed.

The disclosure presents improvements related to the above.

SUMMARY

The techniques of this disclosure generally relate to trays, packaging systems and method for delivery devices and components for a transcatheter stented prosthesis, such as a stented prosthetic heart valve. Various embodiments include a tray having a bath that serves a dual function in supporting the delivery device in a packaged state and can be inverted to hold fluid during loading of the prosthesis while the delivery device is supported in the tray. Various embodiments can also include one or more clips that maintain the delivery device onto the tray but allow for longitudinal movement, which is beneficial during loading of the prosthesis. Various embodiments can also include one or more recesses for positioning of an indeflator having a fluid line or tubing.

In one aspect, the present disclosure provides a packaging system including a delivery device including a handle assembly and a catheter having a proximal end extending from the handle assembly. The catheter further having a distal end configured to support a prosthesis. The packaging system further includes a tray having an upper surface and a first recess extending into the upper surface. The delivery device is at least partially positioned into the first recess and the first recess terminates at a bath area in which the distal end is positioned. The packaging system also includes a clip on the upper surface and adjacent the bath area and the first recess. The packaging system has a packaged configuration and a loading configuration. The catheter is positioned outside of the first clip in the packaged configuration and the catheter is positioned within the first clip in the loading configuration. Additionally, the catheter can move longitudinally within the clip in the loading configuration.

In another aspect, the disclosure provides a packaging system including a delivery device including a handle assembly and a catheter having a proximal end extending from the handle assembly. The catheter including a distal end configured to support a prosthesis. The packaging assembly further includes a tray including an upper surface. The tray also includes a first recess extending into the upper surface. The delivery device is at least partially positioned into the first recess and the first recess terminates at a bath area of the tray in which the distal end of the catheter is positioned. The packaging assembly also includes a second recess extending into the upper surface and positioned adjacent the bath area, the second recess configured to receive and maintain an indeflator fluid line or tubing.

In yet another aspect, the disclosure provides methods of transitioning a packaging system from a packaged configuration to a loaded configuration. Such methods can include providing a packaging system including a delivery device including a handle assembly and a catheter having a proximal end extending from the handle assembly, the catheter including a distal end configured to support a prosthesis. The packaging assembly also including a tray including an upper surface and a first recess extending into the upper surface. The delivery device is at least partially positioned within the first recess and the first recess terminates at a bath area in which the distal end is positioned. The packaging assembly further has a first clip on the upper surface and adjacent the bath area and the first recess. The catheter is disengaged from the first clip in a packaged configuration. Methods include positioning the catheter within the first clip and longitudinally moving the catheter through the first clip.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician during delivery of a prosthesis. "Distal" or "distally" are a position distant from or in a direction away from the clinician during delivery of the prosthesis. "Proximal" and "proximally" are a position near or in a direction toward the clinician during delivery of the prosthesis.

An example of a packaging system 10 is collectively illustrated in FIGS. 1-7. In this example, the packaging system 10 includes a tray 12 maintaining a delivery device 14. The delivery device 14 can be of any of the type for transfemoral delivery of a prosthesis, such as a prosthetic heart valve. In one example, the delivery device 14 is used for delivering a prosthesis (not shown) including an expandable metal frame valve to a desired implant location, such as by way of, the femoral artery, the femoral vein, the pulmonary vein, a valved conduit, or otherwise.

As referred to herein, a prosthesis or stented prosthetic heart valve useful with the various systems, devices and methods of the present disclosure may assume a wide variety of configurations. Stented prostheses can include, for example, stented prosthetic heart valves ("prosthetic valves"), such as a bioprosthetic heart valve having tissue leaflets or a synthetic heart valve having polymeric, metallic or tissue-engineered leaflets, and can be specifically configured for replacing valves of the human heart. The stented prostheses of the present disclosure may be self-expandable, balloon expandable and/or mechanically expandable or combinations thereof. In general terms, the prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., nitinol). The stent frame can be laser-cut from a single piece of material, or can be assembled from a number of discrete components. Non-limiting examples of suitable prostheses are disclosed in U.S. Pat. No. 10,729,541, the entire disclosure of which is incorporated herein by reference.

Delivery devices that can be used with the systems and methods of the disclosure can take a wide range of configurations and the disclosure is not intended to be limited to any specific device or configuration. In one example, the delivery device 14 can include a handle assembly 16 and at least one elongated, flexible catheter 18 extending from the handle assembly. The catheter 18 can include a proximal end 20a connected to the handle assembly 16 and a distal end 20b on which the prosthesis can be loaded. The delivery device 14 can be configured to be maintained in multiple separated portions within the tray 12 or can be configured to be maintained within the tray 12 as assembled. The catheter can be configured for supporting the prosthesis in a loaded arrangement in which the prosthesis is compressed and maintained on a distal end of the catheter. Various suitable, non-limiting, delivery devices include model numbers M018218C001; M018218C002; and M018218C003 available from Medtronic, Inc. of Minneapolis, Minnesota.

The packaging system 10 is configured to package the delivery device 14 for shipment and storage until use includes the tray 12 having an upper surface 22 and a continuous recess 24 within the upper surface 22 configured to receive and support the delivery device 14. In the illustrated example, the recess 24 is at least partially curved or U-shaped, forming a bend 26 so that the distal end 20b of the catheter 18 is positioned adjacent the handle assembly 16 when the delivery device 14 is positioned within the recess 24. The U-shaped packaged configuration of the delivery device 14 generally allows for a single operator to load the prosthesis onto the delivery device 14. The recess 24 terminates at a bath area 28, which is an additional recessed section extending from the upper surface 22 that includes a reservoir 30 for receiving fluid, such as saline or the like, for loading of the prosthesis onto the distal end 20b of the catheter 18. The tray 12 can further include one or more pockets 32 extending from the recess that provide room for a user's hands to grip, position and/or remove the delivery device 14 from the tray 12. The tray 12 can optionally include one or more accessory pockets 34 provided in the upper surface 22 for the storage of one or more delivery device or loading accessories (not shown).

In some examples, the tray 12 includes a removable bath 38 positioned within the bath area 28. In a packaged arrangement of FIGS. 1 and 5A, the bath 38 is inverted and positioned within the bath area 28 to support the distal end 20b of the catheter 18 in the packaged arrangement. For example, one side of the bath 38, can include a groove 40 that is configured like a clip or is sized to frictionally maintain a position of the distal end 20b. The groove 40 can be continuous or discontinuous (as shown). The opposing side of the bath 38 can include one or more reservoirs 42. Once the delivery device 14 is to be used, the catheter 18 can be removed from the groove 40 and put into the bath area 28 after removal of the bath 38. The bath 38 can be flipped over (i.e. reverted after disconnecting from the bath area 28 of the recess 24 so that at least one reservoir 42 can be filled with fluid, such as saline, to wash the prosthesis, at an area removed from the tray 12. In some examples, the bath 38 is secured to the bath area 28 to prevent movement of bath 38 until use.

Figure 1:
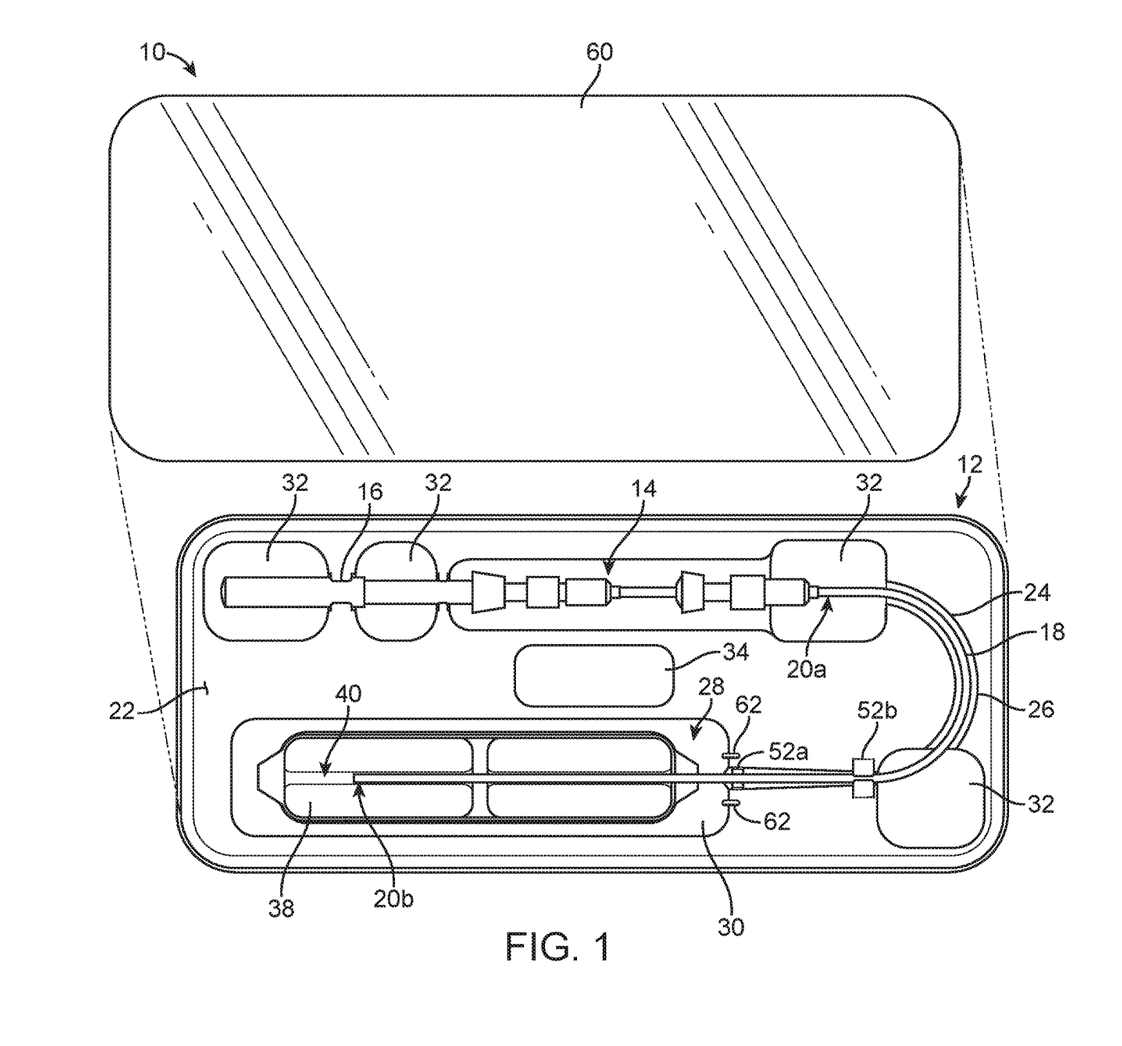
FIG. 1 is a top view of a packaging system including a delivery device having a cover of the packaging system shown removed for ease of illustration.
Figure 2:
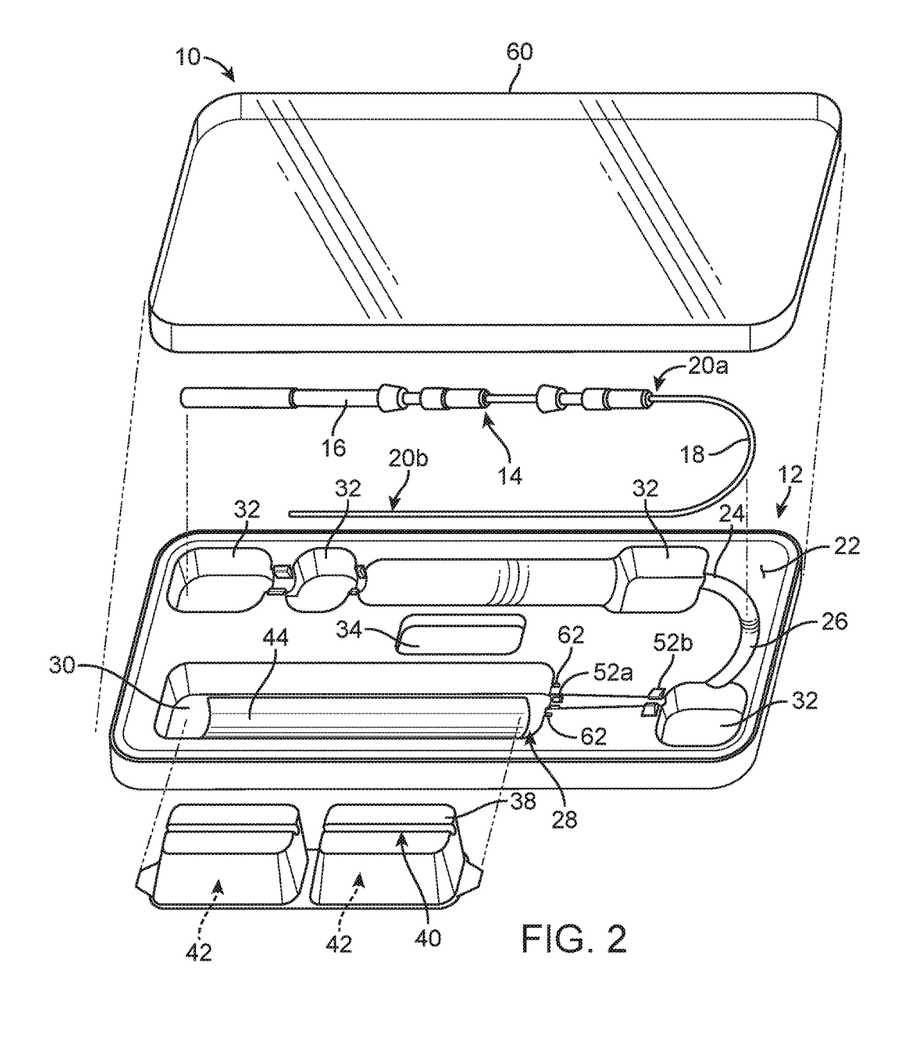
FIG. 2 is an exploded view of the packaging system of FIG. 1.
Figure 3:
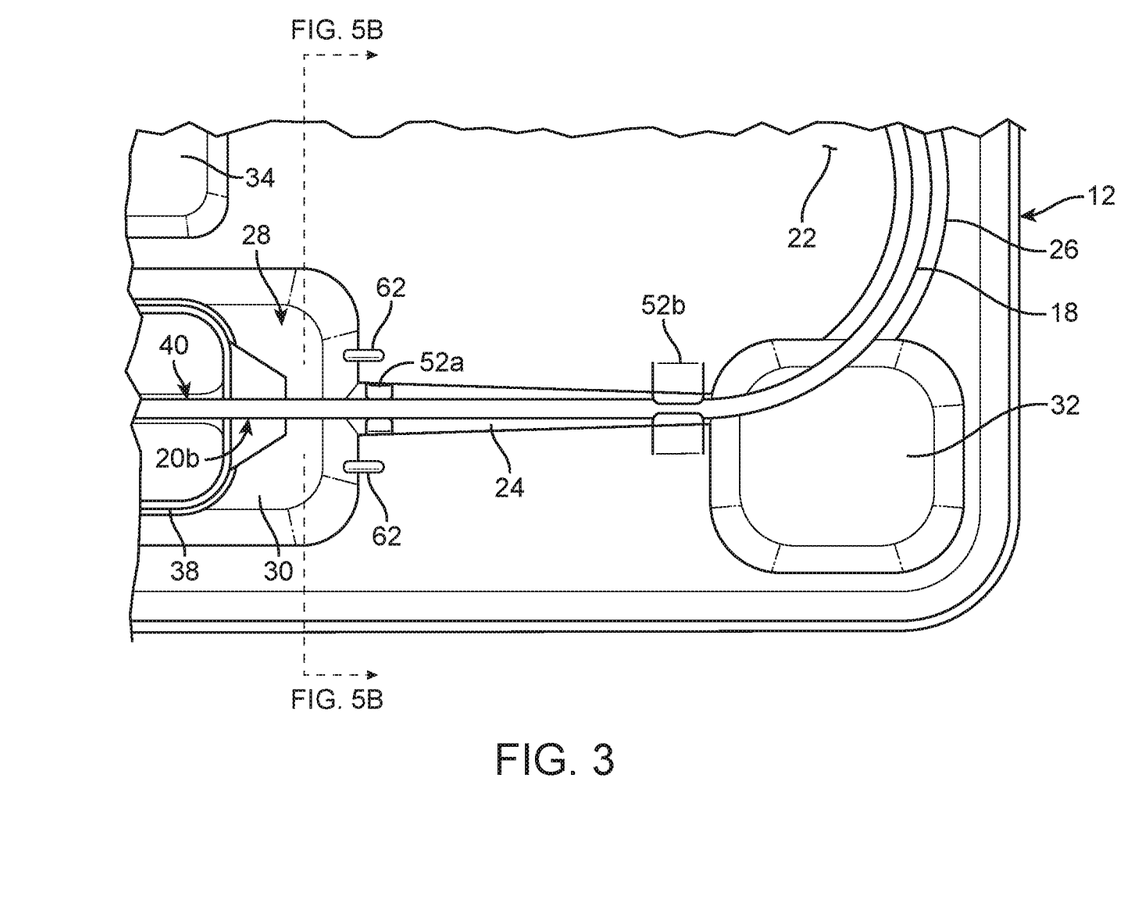
FIG. 3 is a partial, top view of the packaging system of FIG. 1.
Figure 4:
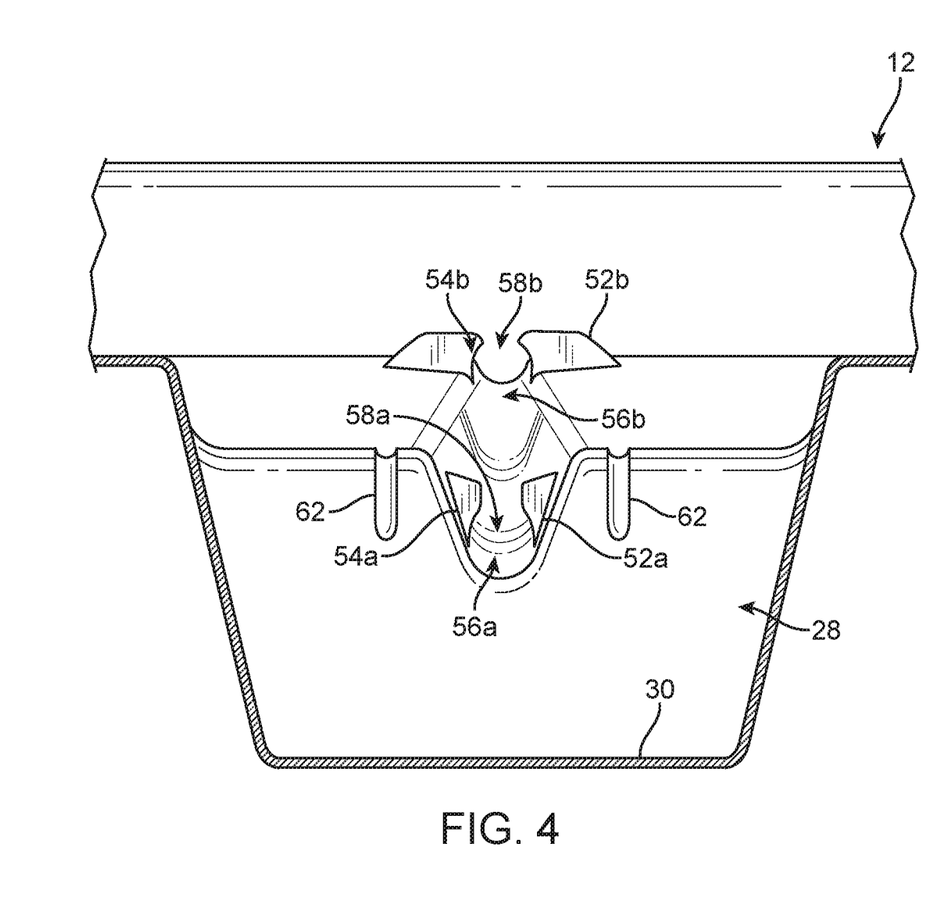
FIG. 4 is a cross-sectional view of the packaging system of FIG. 1 having first and second clips with the delivery device omitted for ease of illustration.
Figure 5A:
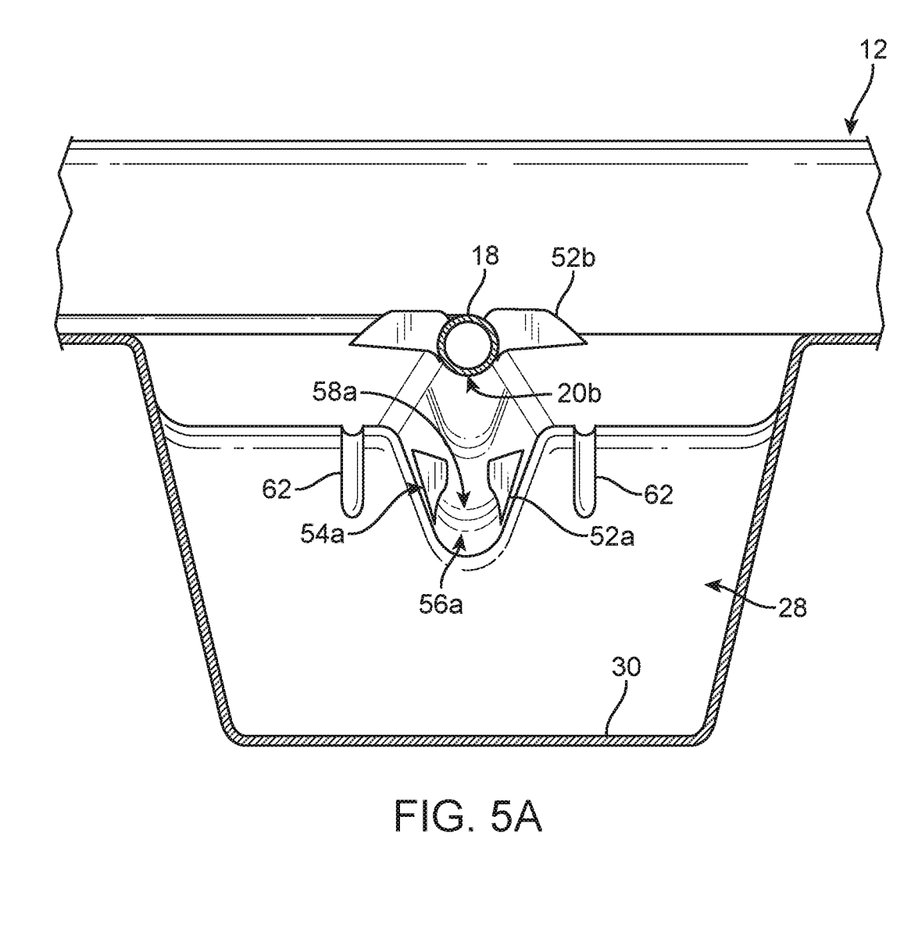
FIG. 5A is a partial, cross-sectional view of the packaging system of FIGS. 1-3 in the packaged configuration.
Figure 5B:
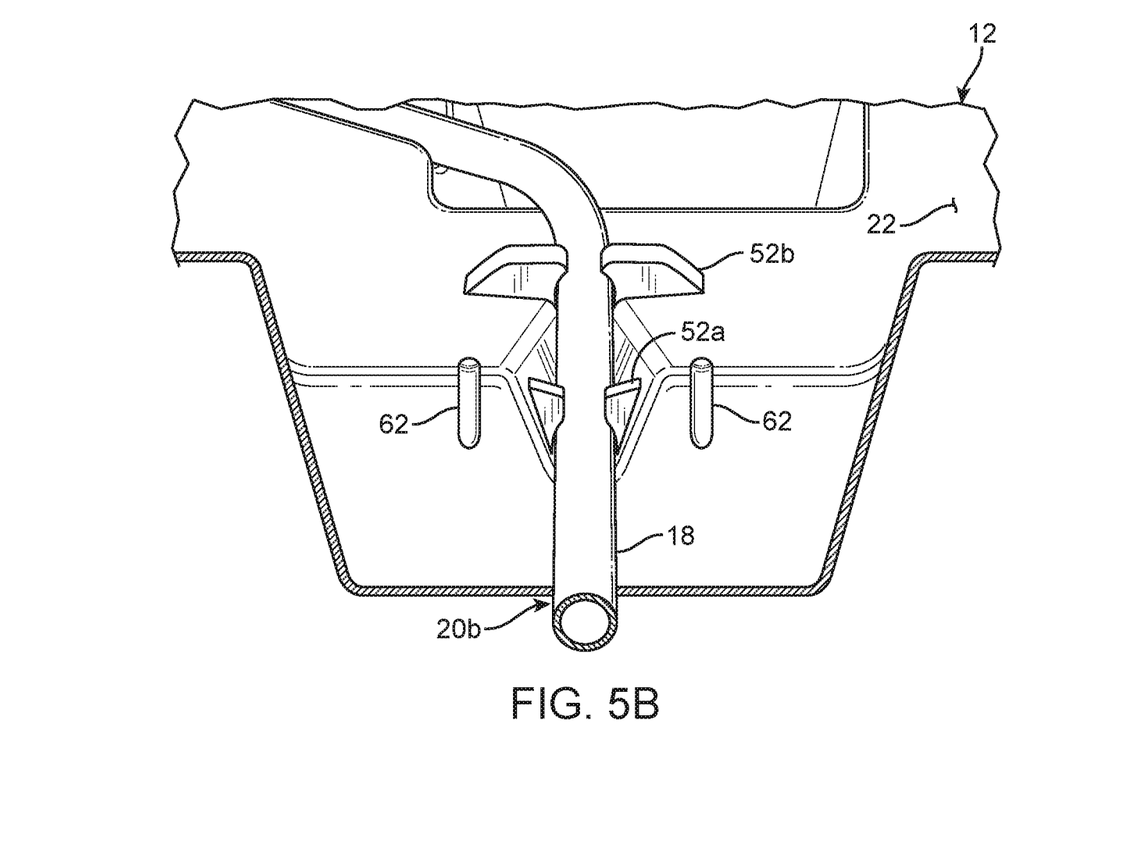
FIG. 5B is a partial, cross-sectional view of the packaging system of FIGS. 1-3 and 5B in a loading configuration as viewed along line 5B-5B of FIG. 3.
Figure 6:
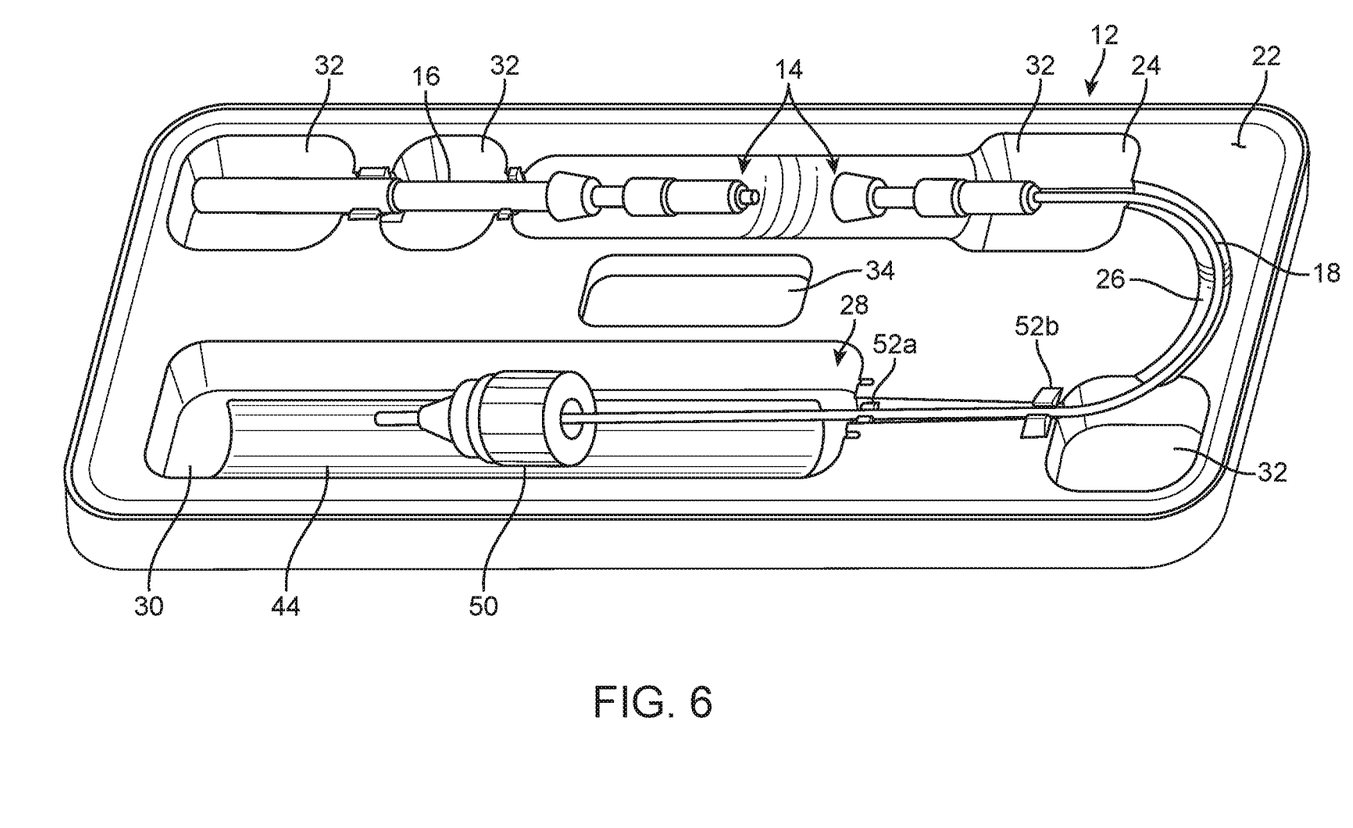
FIG. 6 is a partial, perspective view of the packaging system of FIG. 1 in the loading configuration.

In various embodiments, as perhaps best shown in FIG. 6, the reservoir 30 can optionally include a radiused bottom section or surface 44 extending along at least a portion of the length of the reservoir 30. The bottom surface 44 can define a radius corresponding to a funnel loading system 50 configured for loading the prosthesis onto the distal end 20b. The funnel loading system 50 may be of any known and used in the art. One non-limiting example is model number D00320694 available from Medtronic, Inc. of Minneapolis, Minnesota.

The tray 12 can include additional features for positioning the catheter 18. For example, the tray 12 can include one or more clips 52a, 52b (e.g., two clips). Each clip 52a, 52b need not be identical and may vary depending on its intended function and/or position on the upper surface 22. The first clip 52a can be positioned adjacent the bath area 28. In one embodiment, each of the clips 52a, 52b is configured to maintain the catheter 18 within the respective clip 52a, 52b while allowing longitudinal movement of the catheter 18 within the respective clip 52a, 52b. In one example, each clip 52a, 52b can include a receiving end 54a, 54b connected to an engagement end 56a, 56b collectively defining an open area 58a, 58b. The receiving end 54a, 54b may be tapered so that the open area 58a, 58b is correspondingly tapered. The engagement end 56a, 56b may define a cross-section that corresponds with a cross-section of the catheter 18. In various examples, both of the open areas 58a, 58b at the respective engagement ends 56a, 56b define round cross sections corresponding with a round cross-sectional shape of the catheter 18 so that the catheter can slide longitudinally through the open areas 58a, 58b at the engagement ends 56a, 56b while being maintained within the respective clip 52a, 52b. To engage the catheter 18 with the first clip 52a, the catheter 18 is pushed through open area 58a, 58b from the receiving end 54a, 54b and into engagement end 56a, 56b. The second clip 52b can be positioned along the recess 24 adjacent the bend 26, for example. The tapered configuration of the receiving ends 54a, 54b, in some examples of the disclosure, are configured to resist movement of the catheter 18 out of the respective engagement end 56a, 56b once the catheter 18 is positioned within the open area 58a, 58b at the engagement end 56a, 56b.

In various embodiments, the packaging system 10 includes a packaged configuration (see, e.g., FIGS. 1 and 5A) in which the catheter 18 is positioned outside of the first clip 52a and within the engagement end 56b of the second clip 52b. In the packaged configuration, the catheter 18 can move longitudinally with respect to the first and second clips 52a 52b. With respect to the second clip 52b, the catheter 18 can slide longitudinally within the open area 58b in the packaged configuration. In some examples, the catheter 18 is not engaged at all with the first clip 52a in the packaged configuration. The packaging system 10 further includes a loading configuration (see, e.g., FIGS. 5B and 6-7) in which the catheter 18 is pushed through the open area 58a from the receiving end 54a of the first clip 52a into the engagement end 56a of the first clip 52a so that the catheter 18 is maintained within the first clip 52a. This engagement will transition the distal end 20b of the catheter 18 to increase an angle formed between the upper surface 22 and the distal end 20b so that the distal end 20b is angled toward the bottom surface 44 of the bath area 28. In the loading configuration, the catheter 18 is maintained within the first and second clips 52a, 52b but can slide longitudinally through both of the first and second clips 52a, 52b at the engagement end 56a, 56b. In the loading configuration, the bath 38 is removed from the bath area 28 and the bath area 28 is further at least partially filled with fluid, such as saline.

The packaging system 10 can additionally include a cover 60 for removably positioning over the tray 12 in the packaged configuration that can be of many types and the present disclosure is not intended to be limited to any particular cover configuration. In one example, the cover 60 is configured like a pouch to fully encapsulate the tray 12. The cover 60 is generally configured to maintain sterility of any contents of the tray 12 while also further maintaining the delivery device 14 and/or any optional accessories provided in position within the packaging system 10, if desired. The cover 60 may include a single or multiple components or structures suitable for obtaining these objectives.

Figure 7:
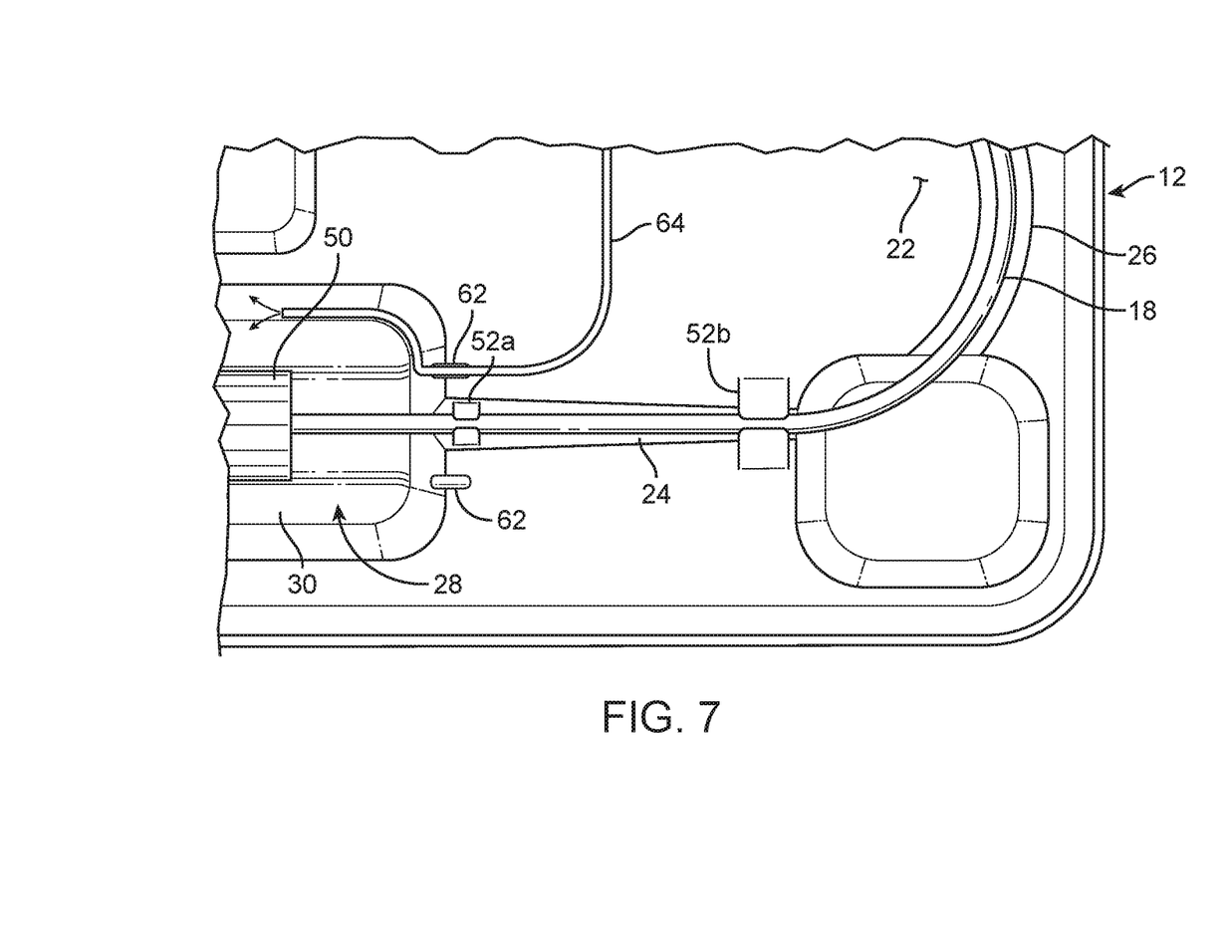
FIG. 7 is a partial, top view of the packaging system of FIG. 1 in the loading configuration.

As is perhaps best shown in FIG. 7, various embodiments can further include additional recess(es) 62 to receive and position an indeflator fluid line 64. One example of a suitable indeflator having such a fluid line or tubing is model number IN8140 available from Merit Medical of South Jordan, Utah.

Various methods of use include methods of transitioning a packaging system (e.g., packaging system 10) from a packaged configuration to a loaded configuration. Such methods can include providing the packaging system including the delivery device including the handle assembly and the catheter having the proximal end extending from the handle assembly, the catheter including the distal end configured to support a prosthesis of the type disclosed herein. The packaging assembly also including the tray having the upper surface and the first recess extending into the upper surface. The delivery device is at least partially positioned within the first recess and the first recess terminates at the bath area in which the distal end is positioned. The packaging assembly further has the first clip on the upper surface and adjacent the bath area and the first recess. If present, the cover can be removed. The catheter is disengaged from the first clip in the packaged configuration. Methods can include positioning the catheter within the first clip and optionally longitudinally moving the catheter through the first clip. The method also includes providing the prosthesis and loading the prosthesis onto the catheter of the delivery device. In some methods, the packaging system further includes the bath positioned within the bath area in the packaged configuration. The bath can have a groove that frictionally maintains the distal end of the catheter in the packaged configuration. Such methods can further include removing the catheter from the groove and removing the bath from the bath area. Various methods include filling the reservoir of the bath area with fluid prior to loading the prosthesis. In some examples, the tray further includes the second clip; wherein the catheter is engaged with the second clip in the packaged configuration. In some examples, the catheter can longitudinally slide though the second clip in the packaged configuration. In various examples, the tray further includes the second recess positioned adjacent the bath area and methods can further include positioning the indeflator fluid line within the second recess and the bath area.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A packaging system comprising:
   a delivery device including a handle assembly and a catheter having a proximal end extending from the handle assembly, the catheter further having a distal end configured to support a prosthesis; and
   a tray including:
      an upper surface,
      a first recess extending into the upper surface, the delivery device at least partially positioned into the first recess; wherein the first recess terminates at a bath area in which the distal end is positioned, and
      a clip on the upper surface and adjacent the bath area and the first recess,
   wherein the packaging system has a packaged configuration and a loading configuration,
   wherein the catheter is positioned outside of the first clip in the packaged configuration and the catheter is positioned within the first clip in the loading configuration;
   further wherein the catheter can move longitudinally within the clip in the loading configuration.

2. The packaging system of claim 1, wherein the first recess is configured to maintain the catheter in a U-shape.

3. The packaging system of claim 1, further comprising a bath having a groove for receiving the distal end of the catheter in the packaged configuration, the bath including a reservoir positioned opposite the groove.

4. The packaging system of claim 1, wherein the clip includes a tapered receiving end connected to an engagement portion collectively defining an open area, wherein the catheter is positioned in the open space of the engagement end in the loading configuration.

5. The packaging system of claim 1, wherein the tray includes a second clip, wherein the catheter is positioned within an open area of the second clip in the packaged and loading configurations; wherein the catheter can move longitudinally within the open area of the second clip in both of the packaged and loading configurations.

6. The packaging system of claim 1, wherein the upper surface includes a second recess positioned adjacent the bath area that is configured to receive and maintain a position of a fluid line.

7. The packaging system of claim 1, further comprising a cover positioned over and covering the upper surface of the tray.

8. A packaging system comprising:
   a delivery device including a handle assembly and a catheter having a proximal end extending from the handle assembly, the catheter including a distal end configured to support a prosthesis; and
   a tray including an upper surface:
      a first recess extending into the upper surface, the delivery device at least partially positioned into the first recess; wherein the first recess terminates at a bath area of the tray in which the distal end of the catheter is positioned, and
      a removable bath insert configured to be disposed in the bath area, the removable bath insert including a first side including a reservoir and a second side including a groove, wherein in a packaged configuration the removable bath insert is disposed in the bath area with the first side facing the upper surface of the tray and the distal end of the catheter is positioned in groove, and wherein in a loading configuration the removable bath is configured to be removed from the bath area.

9. The packaging system of claim 8, wherein the tray further comprises a second recess extending into the upper surface and positioned adjacent the bath area, the second recess configured to receive and maintain an indeflator line.

10. The packaging system of claim 9, further comprising an indeflator line positioned within the second recess.

11. The packaging system of claim 8, further comprising a first clip on the upper surface adjacent the bath area; wherein in the packaged configuration the catheter is positioned outside of the first clip and wherein in the loading configuration the catheter is maintained within the first clip; wherein the catheter can move longitudinally within the first clip in the loading configuration.

12. The packaging system of claim 11, wherein the tray includes a second clip, wherein the catheter is positioned within the second clip in the packaged and loading configurations; wherein the catheter can move longitudinally within the second clip in both of the packaged and loading configurations.

13. The packaging system of claim 11, further comprising a third recess in the upper surface of the tray, wherein the first clip is positioned between the second and third recesses.

14. A method of transitioning a packaging system from a packaged configuration to a loaded configuration, the method comprising:
   providing a packaging system including:
      a delivery device including a handle assembly and a catheter having a proximal end extending from the handle assembly, the catheter including a distal end configured to support a prosthesis; and
      a tray including an upper surface:
         a first recess extending into the upper surface, the delivery device at least partially positioned within the first recess; wherein the first recess terminates at a bath area in which the distal end is positioned, and
         a first clip on the upper surface and adjacent the bath area and the first recess, wherein the catheter is disengaged from the first clip in a packaged configuration;
   positioning the catheter within the first clip; and
   longitudinally moving the catheter through the first clip.

15. The method of claim 14, further comprising providing a prosthesis and loading the prosthesis onto the delivery device.

16. The method of claim 15, wherein the packaging system further includes a bath positioned within the bath area in the packaged configuration, the bath having a groove that frictionally maintains the distal end of the catheter in the packaged configuration, the method further including removing the catheter from the groove and removing the bath from the bath area.

17. The method of claim 16, further comprising filling a reservoir of the bath area with fluid prior to loading the prosthesis.

18. The method of claim 14, wherein the tray further includes a second clip; wherein the catheter is engaged with the second clip in the packaged configuration.

19. The method of claim 18, wherein the catheter can longitudinally slide though the second clip in the packaged configuration.

20. The method of claim 14, wherein the tray further includes a second recess positioned adjacent the bath area, the method further including positioning an indeflator line within the second recess and the bath area.

* * * * *